United States Patent [19]

Brown

[11] 4,173,978
[45] Nov. 13, 1979

[54] SELF CONTAINED ANTISEPTIC APPLICATOR SWAB

[76] Inventor: James B. Brown, R.F.D. #2, Box 313, Mt. Kisco, N.Y. 10549

[21] Appl. No.: 813,496

[22] Filed: Jul. 7, 1977

[51] Int. Cl.² ............................................ A61M 31/00
[52] U.S. Cl. .................... 128/269; 206/438; 206/820; 401/132; 401/196
[58] Field of Search ............... 128/269, 260; 206/531, 206/540, 539

[56] References Cited

U.S. PATENT DOCUMENTS

| 3,179,108 | 4/1965 | Bloch et al. | 128/269 |
| 3,508,547 | 4/1970 | Deuschle | 128/269 |
| 3,876,314 | 4/1975 | Nehring | 401/133 |
| 3,891,331 | 6/1975 | Avery | 128/269 |
| 4,083,451 | 4/1978 | Hair | 206/539 |

Primary Examiner—Robert W. Michell
Assistant Examiner—M. A. Juten
Attorney, Agent, or Firm—Alfred E. Miller

[57] ABSTRACT

An inexpensive disposable antiseptic applicator swab made on a blister forming and sealing machine in which complimentary pockets are made in thermoplastic sheets to form a chamber that receives a crushable glass ampoule containing the antiseptic liquid. The thermoplastic sheets are then heat sealed, leaving an opening into said chamber, said opening being covered by a foam applicator tip through which the antiseptic liquid can penetrate.

5 Claims, 8 Drawing Figures

U.S. Patent  Nov. 13, 1979  4,173,978
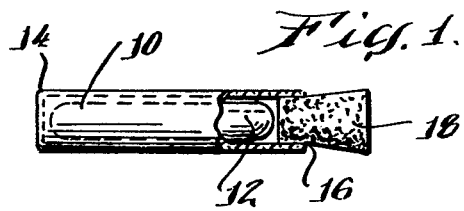
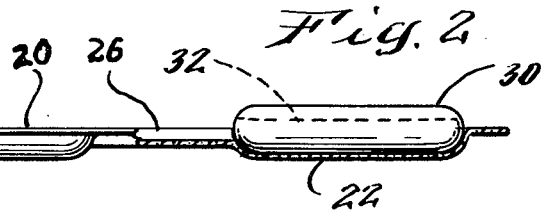
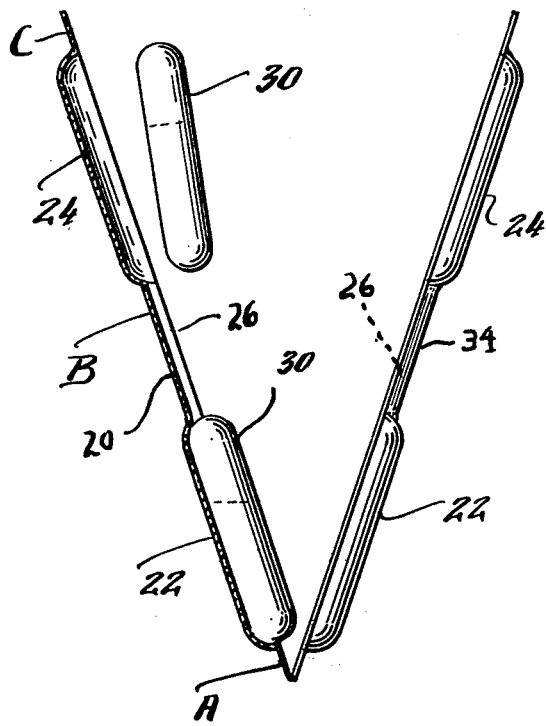
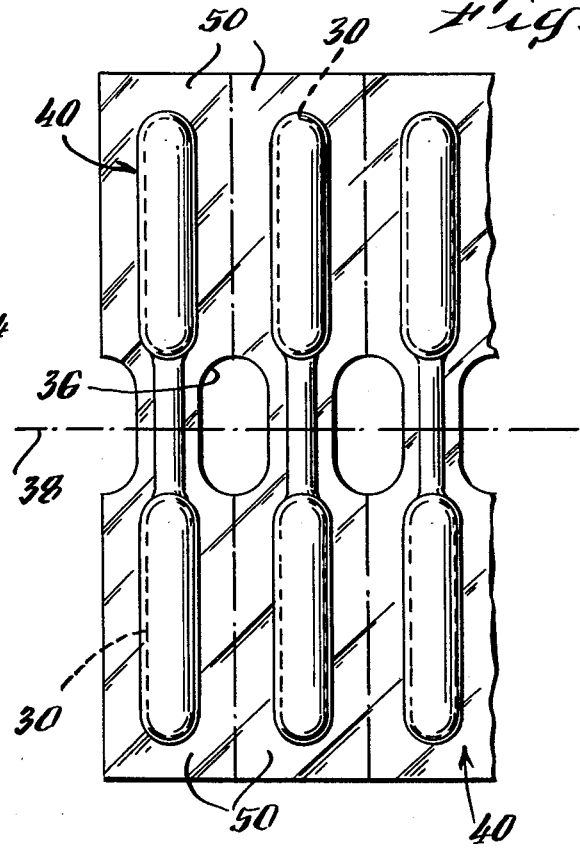
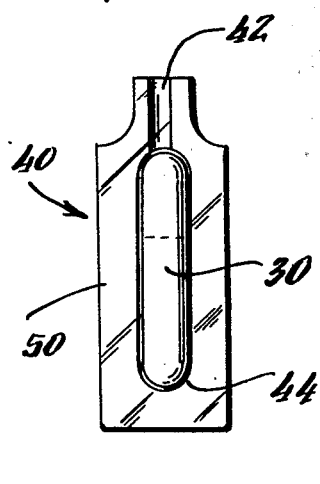
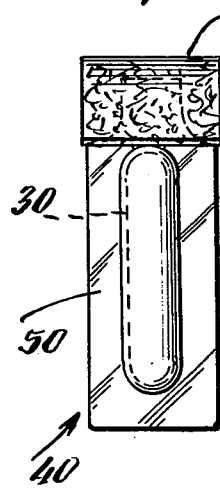
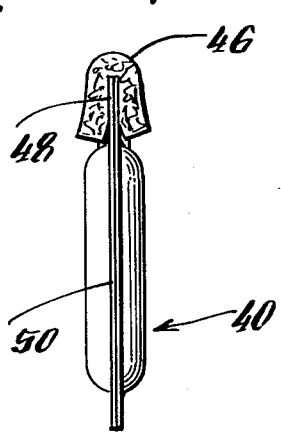
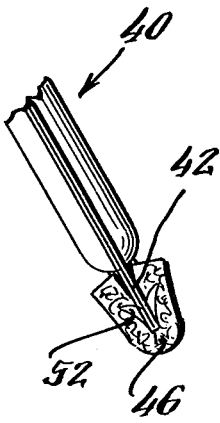

SELF CONTAINED ANTISEPTIC APPLICATOR SWAB

BACKGROUND OF THE INVENTION

The throw away type antiseptic applicator swab is known, however, it has become imperative to reduce the cost of producing the same. The known applicator swab is costly to make and it becomes necessary to eliminate as much hand fabrication as possible.

It is, therefore, an object of the present invention to provide a method for mass production of disposable antiseptic applicator swabs.

It is a further object of the present invention to provide a product resulting from the instant novel method which is easier to handle and has a larger swab surface.

It is another object of the present invention to provide a polyester foam tip that is secured to a plastic blister encasing in a chamber the crushable glass ampoule at a place where there is an opening to the chamber, the foam tip being affixed over the opening by means of a porous adhesive backing.

A further object of the present invention, and an alternate embodiment thereof, is to heat seal the foam tip to the plastic bubble package.

Still another object of the present invention is to provide a spike-like configuration adjacent to the mouth or opening into the plastic bubble whereby the foam tip can be inserted therein and rigidly held thereby.

In order that the invention will be more clearly understood, it will now be disclosed in greater detail with reference to the accompanying drawings, in which:

FIG. 1 is an elevational view of a prior art antiseptic applicator swab;

FIG. 2 is a sectional view showing a web or sheet of vacuum formable plastic material in which pockets are formed for receiving a glass ampoule and constructed in accordance with the teachings of the present invention;

FIG. 3 is a sectional view showing glass ampoules in the pockets of the web of vacuum formable plastic material, and about to be encased therein;

FIG. 4 is a top plan view of a series of pairs of plastic blisters as part of a continuous line and showing a die cutter punching out sections of the webbing on opposite sides of each blister pair, and making a transverse cut to sever the top and bottom plastic blisters;

FIG. 5 is a longitudinal sectional view taken through a single plastic blister;

FIG. 6 is a front elevational view of a single plastic blister having the glass ampoule therein and with a foam applicator tip attached thereto;

FIG. 7 is a side elevational view of the structure and arrangement of FIG. 6; and FIG. 8 is a partial sectional view of an alternate means for securing the foam applicator tip to the plastic blister.

DESCRIPTION OF THE PREFERRED EMBODIMENTS

A known antiseptic applicator swab is shown in FIG. 1 in which a glass ampoule 10 containing the antiseptic liquid 12 is inserted in a plastic sleeve 12 having a closed end 14 and an open end 16. A cotton plug tip 18 is inserted in the open end and sealed preferably by applying acetone which melts the plastic to the cotton plug. The assembly of the known applicator swab was accomplished by hand and therefore was costly to make.

In order to significantly reduce the cost of manufacture of antiseptic applicator swabs, the method and resulting product shown in FIGS. 2-7 were devised; it being noted that the antiseptic swab outer container can be manufactured on a blister forming and sealing machine.

As seen in FIG. 2, a single web 20 of a vacuum formable plastic sheeting or polyvinylchloride, polyethylene, buterate, or the like, is used having a thickness in the order of 0.015 inches. The web 20 is provided with two pockets 22 and 24, and recessed opening or channel 26. The pockets 22 and 24 each of which form a chamber and each receive a crushable glass ampoule 30 having antiseptic liquid 32 therein, for example, tincture merthiolate. After the glass ampoules are in place in their respective pockets, an identical and complimentary single web 34, as shown in FIG. 3, is placed over web 20 so that the ampoules are completely enclosed in a blister package as particularly seen in FIG. 4. The blister package is of sufficient thickness to prevent the fractured glass of the ampoule from penetrating through the blister when the applicator is crushed by the user.

As seen in FIG. 3, each pair of blisters are heat sealed at points A, B and C respectively, and when sealed, take on the appearance of the structure shown in FIG. 4 with the blister packages in pairs and in a continuous line.

A die cutter (not shown) performs an operation on the line of blister packages so that an oval-shaped area 36 is cut out on opposite sides of each blister pair. In addition, a transverse cut 38 is made along the continuous line of blister packages.

After the foregoing process is accomplished, each resultant blister package, referred to generally by the numeral 40 and clearly seen in FIG. 5, is provided with an opening 26 in the plastic bubble outer enclosure that forms a channel 42 for the pockets of the webs forming a chamber 44.

A foam tip 46, as seen in FIGS. 6 and 7, is preferably of a two pound density polyester foam and is provided with an adhesive strip 48 that is adhesive both on the front and back, and is porous so that the antiseptic liquid 32 can penetrate therethrough when the glass ampoule 30 is crushed and the antiseptic liquid flows through the channel 42 in the blister package and into the foam tip 46. The adhesive is of the type known as Micropore adhesive, a registered trademark of the 3M Company, and will not lose its adhesiveness when exposed to the alcohol present in the antiseptic.

As seen in FIG. 5, a part of the semi-oval shaped area punched out by die cutter 36 forms a cut away section and eliminates sharp edges on the sides of the flat part 50 of the applicator adjacent to the foam tip 46. This cut away construction prevents the scratching or cutting of the user of the applicator swab.

It is also to be noted that the foam tip 46 can be applied to the blister package by heat sealing, instead of using an adhesive backing for the foam tip.

FIG. 8 shows another embodiment of the present invention in which the top of the blister package 40 is provided with a spike configuration 52 surrounding the channel 42 in the blister package. The foam tip 46 is impaled upon the spike, thus reliably securing the same without the use of heat sealing or an adhesive.

It should be readily apparent that because of flat part 50 of the blister package 40 there is less likelihood that the antiseptic applicator swab will slip out of the user's fingers, as might occur when the applicator is cylindrical. Thus, the present device is easier to handle, and the extended foam area results in the desirable larger swab surface.

What is claimed is:

1. A disposable antiseptic applicator swab manufactured on a blister forming and sealing machine comprising: a cylindrical crushable glass ampoule having antiseptic liquid therein, a plastic blister package having identical complimentary parts forming a chamber and a flange section, the latter being provided with a channel extending from said chamber to the edge of said flange, said flange having undercut portions at the side edges of said flange adjacent to said channel, the cross section of said blister chamber being slightly larger than the cross section of said ampoule resulting in a relatively tight fit of said ampoule in said blister chamber, and an elongated applicator foam tip folded over said flange at the end thereof having said channel and in communication with the latter so that said antiseptic liquid will penetrate said foam tip when said glass ampoule is crushed, the width of said elongated applicator pad being greater than the width of said flange having the channel therein to prevent contact of the edges of said flange with the channel therein from contact with a patient.

2. The combination as claimed in claim 1 wherein said means for securing said tip is a porous adhesive backing on said foam tip.

3. The combination as claimed in claim 1 wherein said means for securing said tip is a spike formed on said blister package surrounding said opening which impales said foam tip thereon.

4. The combination as claimed in claim 1 wherein said means for securing said tip is a heat seal for said foam tip on said blister package.

5. The combination as claimed in claim 1 wherein said foam tip is a two pound density polyester foam.

* * * * *